United States Patent [19]

Genis

[11] Patent Number: 5,090,409
[45] Date of Patent: Feb. 25, 1992

[54] SINGLE BAG THERAPEUTIC PACK

[76] Inventor: Daniel Genis, 7515 Woodrow Wilson Dr., Los Angeles, Calif. 90046

[21] Appl. No.: 663,606

[22] Filed: Mar. 4, 1991

[51] Int. Cl.$^5$ .................................................. A61F 7/08
[52] U.S. Cl. ........................................ 128/402; 62/530
[58] Field of Search ............... 128/402, 403, 379, 380, 128/82.1, 400; 62/530; 383/901, 44, 80

[56] References Cited

U.S. PATENT DOCUMENTS

| | | | |
|---|---|---|---|
| 3,951,127 | 4/1976 | Watson et al. | 128/403 |
| 4,149,541 | 4/1979 | Gammons et al. | 128/402 |
| 4,592,358 | 6/1986 | Westplate | 128/402 |
| 4,910,978 | 3/1990 | Gordon et al. | 62/530 |

FOREIGN PATENT DOCUMENTS

| | | | |
|---|---|---|---|
| 2632088 | 7/1977 | Fed. Rep. of Germany | 128/403 |
| 334349 | 9/1930 | United Kingdom | 383/901 |

*Primary Examiner*—Edward M. Coven
*Assistant Examiner*—Mark S. Graham
*Attorney, Agent, or Firm*—Roger A. Marrs

[57] ABSTRACT

A therapeutic wrap is disclosed herein for applying heat or cold compression to a body or limb area, which includes a single waterproof bladder, casing or envelope having coupling straps for securing the wrap to the body or limb. The bladder is provided with multiple compartments formed by heat-sealed buttons or spots in fixed spaced relationship defining a curved passageway compartmentalizing the bladder interior. A twist cap permits introduction of a heated, cooled or iced medium such as a solid or fluid into the passageway. The bladder or casing includes a fabric composed of a combination of nylon fabric coated with a vinyl thickness presenting an irregular outer surface and a smooth inner surface, and a display area is carried on the exterior surface thereof between adjacent straps. The straps are sewn to the cloth-like roughened surface and a sealing plastic strip covers the stitching for reinforcement and sealing purposes.

2 Claims, 1 Drawing Sheet

SINGLE BAG THERAPEUTIC PACK

BACKGROUND OF THE INVENTION

1. Field of the Invention

The present invention relates to therapeutic wraps and more particularly to a novel therapeutic device useful in the application of heat or cold to various portions of the human body and its appendages. The invention relates to hot and cold packs of single casing or bladder design intended to be fitted about portions of the human body and its appendages so as to effect the application of heat or cold to a desired body area.

2. Brief Description of the Prior Art

In the past, many types of therapeutic devices have been designed to be filled with hot or cold liquid and then be applied to an affected area of the human body for therapeutic purposes. Such conventional devices include the hot water bag in which a bladder is filled with hot water and then placed against the body area intended to be relieved. Another of the basic types of prior devices includes ice packs in which a bladder is filled with ice and then applied to the affected area.

Difficulties and problems have been encountered with such conventional devices which stem largely from the fact that it is difficult to secure such devices about the affected area so that the person could freely move about without constantly holding the device in position. Furthermore, it is sometimes difficult for the heat or cold of the medium within the pack or wrap to be transferred to the affected area of the body due to thickness of bladder material or multiple layers of materials. In many instances, the rate of energy transfer is not proportional to the temperature difference between the temperature of the medium and the temperature of the affected area. As an example, ice therapy (Cryotherapy) is one of the most extensive treatments used for athletic injuries by physicians, coaches, trainers and players. Although Cryotherapy is very beneficial, if used incorrectly, frostbite or nerve palsy could result. However, these problems can be decreased by avoiding direct contact of the Cryotherapy on an area and increasing padding or other insulation around the application.

Also, sealing of the bladder or casing is a major problem when pressurized gas such as air is employed or when water is used. The problem is particularly acute when the bladder must be stitched or punctured in order to accommodate attachment straps and twist caps.

Therefore, a long standing need has existed to provide a single bag or casing therapeutic wrap for applying hot or cold temperature from a suitable enclosed medium to an affected area of the human body so that the rate of energy transfer is proportional to the temperature difference between the two surfaces. Preferably, such energy transfer is achieved by conduction accomplished by direct contact of the temperature agent with the body surface.

SUMMARY OF THE INVENTION

Accordingly, the above problems and difficulties are obviated by the present invention which provides a novel therapeutic wrap having means for transferring energy by conduction wherein the rate of energy transfer is proportional to the temperature difference between the two surfaces. Such a therapeutic device includes a casing or bladder having a plurality of compartments defined by heat seal spots or barriers which provide an irregular path throughout the interior of the bladder. Hot or cold medium is placed in the passageway compartments of the bladder via a removable twist cap so that the casing prevents direct skin contact of the human body from direct contact with the hot or cold medium. The bladder or casing includes a plurality of seven straps adapted to extend longitudinally along the length of the casing and terminate at its opposite ends in a closure such as a hook and pile construction. Sealing means are provided for waterproofing the casing and the stitched strap construction and the twist cap construction.

The bladder or casing provides a single unitary bag construction when the medium has been introduced into the interior compartments. The outer surface of the casing is rough and has a cloth-like texture while an inner smooth surface is placed directly against the affected body portion of the user so that transfer of hot or cold energy is by conduction and the rate of transfer is proportional to the temperature difference between the surfaces.

Therefore, it is among the primary objects of the present invention to provide a single casing, bladder or bag therapeutic means of unitary construction comprising interior compartments for holding a hot or cold medium in position about portions of the human body, such as appendages or the like.

Another object of the present invention is to provide a novel single bag therapeutic wrap that may be readily secured about human body appendages for applying hot or cold transfer of energy to affected areas for therapeutic purposes with improved sealing means for waterproofing the wrap.

Still another object of the present invention is to provide a novel low-cost single bag therapeutic means adapted to apply either hot or cold compression to an affected area of the human body and which employs heat sealing techniques to provide sealing spots for dividing the interior into multiple compartments.

Still a further object of the present invention is to provide a novel single-component therapeutic wrap wherein an inner compartment encloses a hot or cold medium and wherein the inner surface is smooth and the outer surface is of cloth-like texture such as nylon fabric impregnated with vinyl.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

DESCRIPTION OF THE PREFERRED EMBODIMENT

Figure 1:
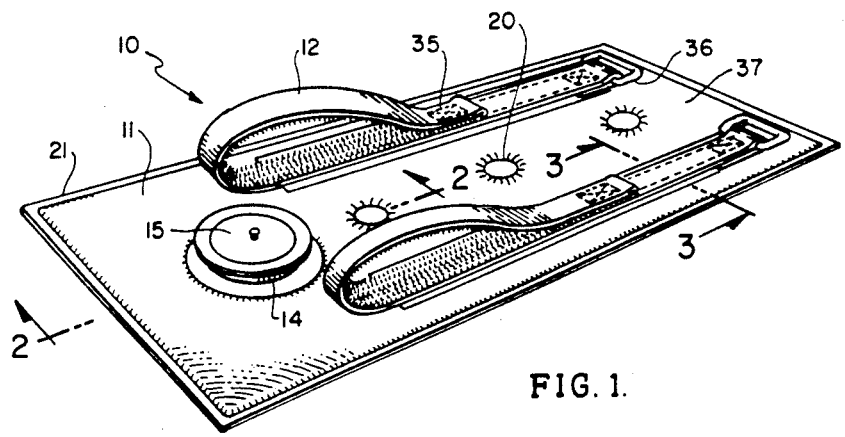
FIG. 1 is a perspective view showing the novel single bag therapeutic wrap of the present invention.

Referring to FIG. 1, the novel therapeutic device of the present invention is illustrated in the general direction of arrow 10 wherein the device includes a single bag, bladder or casing 11 that is disposed about the thigh, leg, shoulder or other body part of the user and wherein the device is releasably held in place by a plurality of straps, such as strap 12. The opposite ends of each strap terminate in a closure means for releasably securing the straps together. In the present instance, the closure means takes the form of a hook and pile fastener so that registration of the straps is not necessary in order to effect closure such as would be the case in the event that buckles or snaps were to be used.

It can be seen that the casing includes an open collar or socket 14 covered by a removable cap 15 through which a hot or cold medium, such as a liquid, is introduced into the bladder. Upon closing, the cap is sealed and the medium is contained therein. The bag, bladder or casing further includes a plurality of compartments or partitions, such as indicated by numerals 16 and 17, that are arranged in fixed spaced-apart relationship extending inwardly from opposite inner surfaces of the bag or bladder.

The disposition of the barriers or walls forms a torturous path or curve defining a passageway along the full length of the bladder. The hot or cold medium occupies this passageway which is continuous along its length. Therefore, an extended path or passageway for the medium is defined as opposed to a single compartment which is occupied by the fluid or medium.

Figure 2:
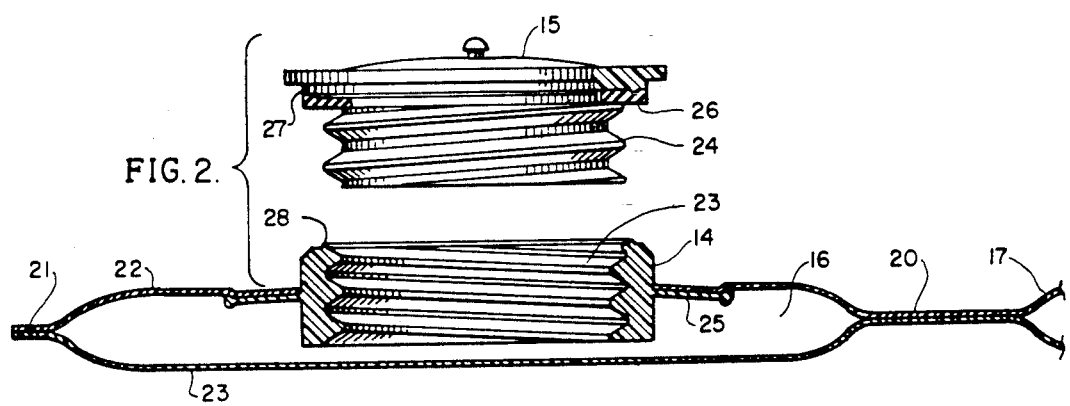
FIG. 2 is an exploded sectional view showing the casing, bladder or bag in accordance with the present invention.

It can also be seen in FIG. 2 that the straps are arranged along the length of the casing 11 and that one end of the closure means, such as indicated by numeral 17, extends over the end of the casing so that it may be folded over upon the opposite end of the strap through an eyelet 18 for coupling with the other half of the closure means. A display area 20 is included on the external surface of the casing so that advertising, alpha/numeric or graphic subject matter can be placed thereon. It is understood that the surface of the covering, represented by numeral 21, is the inner surface adapted to contact the skin or body of the user.

Figure 3:
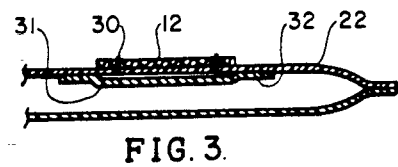
FIG. 3 is an enlarged sectional view of the casing shown in FIG. 2 as taken in the direction of arrows 3—3 thereof.

Referring now in detail to FIG. 3, the casing is illustrated wherein it can be seen that the zippered opening 13 runs along the exterior surface of the casing between the opposite ends of the rectangular or elongated configured casing. When the zipper has been moved to its open position, the bladder 14 will readily slide through the opening into the interior of the casing.

Figures 4, 5:
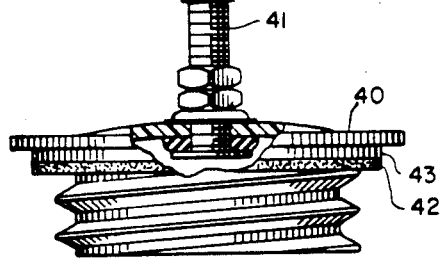
FIG. 4 is an enlarged sectional view of the casing showing the cloth-like fabric.
FIG. 5 is an elevational view of an alternate twist cap.

Referring now in detail to FIG. 4, it can be seen that the edges of the casing are formed with an inner seam 22 which joins material together to close the casing so as to define an interior compartment 23 for receiving the bladder 14. Therefore, the edges are smooth and rounded and sharp seams or edges of material are not pressed against the skin or body of the user.

In FIG. 5, the bladder is illustrated with the cover for the pillow valve opened, as illustrated in dotted lines, so that a fluid medium of either hot or cold temperature can be placed inside the bladder. The various walls or partitions can be provided by heat-sealing the vinyl material of the bladder so that the torturous passageway between the opposite end of the elongated bladder is defined.

FIG. 6 shows a typical wall 16. Preferably, the corners of the bladder are rounded so as to permit ready insertion of the bladder through the unzippered opening 13 in the casing.

When it is desired to use the therapeutic device of the present invention, either ice, cold water or hot water as a medium can be introduced into the vinyl bag 14 through an opened pillow valve 15. The pillow valve has been secured and the outside of the bladder has been towel dried so as to remove any of the medium that may have spilled on the outside of the bladder. Preferably, for the user's safety, the temperature of ice water should not fall below 36° F. while hot water should not exceed 110°. The vinyl bag or bladder containing the medium is introduced into the outer fabric casing 11 through the unzippered opening 13, making sure that the pillow valve of the vinyl bag is at the opening of the outer bag or casing. Next, the therapeutic wrap is positioned about the joint or muscle or body portion of the user and securement is achieved by means of the straps so that a snug fit is produced. Preferably, the user should permit the wrap to remain on the injured body portion for approximately 15 minutes for either hot or cold application and, preferably, this is recommended one to three times per day.

Many different shapes and forms of the thermal wrap are envisioned and such additional shapes, configurations and forms encompass all phases of therapy treatment for a majority of acute and chronic sub-acute injuries. The inventive concept provides portable and reusable thermotherapy-Cryotherapy wraps which offer superior effectiveness, compression, support and comfort. The inventive concept also is designed to provide the user with freedom of mobility and to avoid restriction of the user to a bed or table during the treatment.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

FIGS. 1 and 2 illustrate the placement of heat seal spots or buttons, such as identified by numeral 20, which are employed to divide the interior of the casing or bladder 11 into a plurality of compartments. Button or spot 20 separates compartments 16 and 17 and the disposition of the spots or buttons forms a tortuous path or divided interior which defines a passageway along the full length of the bladder. The spots serve to hold material in position whether it be a quantity of liquid or solid material, or medium, such as ice. The hot or cold medium occupies these compartments and, therefore, an extended path or passageway throughout the interior of the single bag bladder contains the medium which is defined as a single compartment separated into sub-compartments occupied by the fluid or solid medium. The plurality of buttons or spots restricts movement of ice and prevents water from pooling by creating the plurality of compartments or sub-compartments or pockets. The bag or casing or bladder 11 is formed from a pair of cloth-like sheets which are joined about their peripheral edge by a heat seal that is identified by numeral 21.

Referring now in detail to FIG. 2, it can be seen that one sheet is identified by numeral 22 while its opposite sheet is identified by numeral 23, and that the opposing inner surfaces of sheets 22 and 23 define the respective compartments separated by the barriers or spots 20. The socket or collar 14 includes an interior thread 23 adapted to receive the external threads 24 of the cap 15 and the collar or socket 14 includes an outwardly extending flange 25 that is heat-sealed to the underside of sheets 22 so that the collar or socket is carried thereon. The heat-sealing arrangement provides a waterproof seal and the cap 15 includes an elastomeric seal 26 that rests against a pressure shoulder 27 to ensure waterproof sealing when the seal 26 is pressed against a raised lip 28 carried on the extreme end of the socket or collar 14.

Referring now in detail to FIGS. 3 and 4, it can be seen that the strap 12 is stitched to the upper sheet 22 by means of threaded stitches 30. In order to provide a waterproof seal, an elongated plastic strip 31 is placed against the inner surface of the sheet 22 so as to cover the stitching which protrudes through the sheet. The surrounding and peripheral edges of the strip 31 are heat sealed to provide waterproof sealing and the heat seal is indicated by numeral 32.

Referring now in detail to FIG. 4, a greatly enlarged portion of top sheet 22 is illustrated wherein a trough-like construction results from employing a fabric composed of nylon which is coated with a vinyl material providing a thickness of approximately 35 millimeters. This provides a smooth vinyl inside surface, indicated by numeral 33, and a roughened or irregular surface on the outer side, represented by numeral 34. The warp and the weft of the fabric is indicated on the outer side of the sheet, while the smooth vinyl surface is on the inside of the sheet. By providing the PVS plastic socket 14 in heat-sealing relationship with the vinyl smooth inner surface 33 of sheet 22, a waterproof sealing arrangement is provided. Nylon is exposed on the outer surface 34 to provide a protective and non-tear reinforcement.

It can be seen that the straps 12 are arranged along the length of the bag, bladder or casing 11 and that one end of the closure means, such as indicated by numeral 35 in FIG. 1, may extend over the opposite end of the casing so that it may be folded over upon the opposite end of the strap through an eyelet 36 for coupling with the other half of the closure means. A display area is indicated on the outer surface of the sheet 22 by numeral 37 so that advertising, alpha/numeric or graphic subject matter can be disposed thereon. It is understood that the sheet 23 of the covering is the surface adapted to contact the skin or body of the user.

When it is desired to use the therapeutic device of the present invention, either ice in a solid form, cold water or hot water as a medium can be introduced into the nylon fabric bag coated with vinyl through the opening of the socket 14. The cap 15 can readily be removed to permit opening of the socket in order to accommodate the medium passing through. Upon filling, and securement of the cap, the outside of the bladder may be towel dried so as to remove any of the medium that may have spilled on the outside of the bag or bladder. Preferably, for the user's safety, the temperature of ice water should not fall below 36 degrees F, while hot water should not exceed 100 degrees F. Next, the therapeutic wrap is positioned about the joint or muscle area or body portion of the user and securement is achieved by means of the strap 12 so that a snug fit is produced. Preferably, the user should permit the wrap to remain on the injured body portion for approximately 15 minutes for either hot or cold application and, preferably, this is recommended one to three times per day.

Many different shapes and forms of the thermal wrap are envisioned and such additional shapes, configurations and forms encompass all phases of therapy treatment for a majority of acute and chronic sub-acute injuries. The inventive concept provides portable and reusable thermal therapy-Cryotherapy wraps which offer superior effectiveness, compression, support and comfort. The inventive concept also is designed to provide the user with freedom of mobility and to avoid restriction of the user to a bed or table during the treatment.

FIG. 5 shows an alternate cap, indicated by numeral 40, which includes a pneumatic valve 41 through which pressurized air or other medium may be introduced into the interior of the bag 11. The alternate cap 40 includes a seal 42 operable against a shoulder 43 in a similar manner previously described. The pressure valve 41 includes a removable cap 44.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A single bag therapeutic wrap for applying compressive thermotherapy and cryotherapy to the body, comprising the combination of:

a casing of flexible material for holding a quantity of a therapeutic medium and having two opposite sheets joined together by a peripheral heat seal defining an internal compartment between opposing inner surfaces;

releasable fastener means carried on one of said sheets of said casing for achieving a fastened condition;

said sheet other than said fastener means carried sheet having an exterior surface adapted for conduction of the temperature of said medium to a localized area of the user;

said casing includes an elongated continuous and tortuous passageway between its opposite ends extending about a plurality of integral barriers defining said passageway;

said barriers defined as heat-sealed spots joining the opposing inner surfaces of said sheets;

said casing composed of applicable material having a closable inlet port for introducing said medium into said internal compartment;

said casing further composed of a fabric material conducting temperature from said liquid medium;

said fastener means includes at least two straps carried across the major length of said casing sheet in parallel spaced-part relationship separated by the central longitudinal axis extending along said casing;

closure means cooperatively carried on opposite ends of said straps for effecting releasable closure;

said closure means is a hook and pile closure;

said sheets composed of a nylon fabric material coated with a vinyl material defining smooth inner surfaces and an irregular, roughened, fabric textured outer surface and further characterized as being waterproof;

said straps are sewn onto the exterior surface of said fastener means carried sheet by a plurality of stitches; and a vinyl strip covering said stitches having its peripheral edge marginal region heat-sealed directly to said fastener means carried sheet smooth inner surface.

2. The invention as defined in claim 1 wherein:

said closable inlet port includes a flanged collar carried on said sheet stitched with said straps and having a threaded receptacle for threadably receiving a cap having a threaded shank;

said collar terminating with a raised ridge and said cap having an annular shoulder; and an annular resilient seal carried about said shank separating said shoulder from said ridge.

* * * * *